(12) United States Patent
Broderick et al.

(10) Patent No.: US 9,233,928 B2
(45) Date of Patent: Jan. 12, 2016

(54) SYNTHESIS OF LACTAM BASED IONIC LIQUID

(71) Applicant: UOP LLC, Des Plaines, IL (US)

(72) Inventors: Erin M. Broderick, Arlington Heights, IL (US); Alakananda Bhattacharyya, Glen Ellyn, IL (US); Alan B. Levy, Randolph, NJ (US); Lihao Tang, Bridgewater, NJ (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/271,308

(22) Filed: May 6, 2014

(65) Prior Publication Data

US 2015/0322016 A1 Nov. 12, 2015

(51) Int. Cl.
*C07D 223/10* (2006.01)

(52) U.S. Cl.
CPC .................................. *C07D 223/10* (2013.01)

(58) Field of Classification Search
CPC .................................................... C07D 223/10
See application file for complete search history.

(56) References Cited

U.S. PATENT DOCUMENTS

| | | | |
|---|---|---|---|
| 7,220,869 B2 | 5/2007 | Deng et al. | |
| 7,285,698 B2 | 10/2007 | Liu et al. | |
| 2006/0135839 A1 | 6/2006 | Elomari et al. | |
| 2007/0021604 A1 | 1/2007 | Deng et al. | |
| 2007/0142676 A1 | 6/2007 | Elomari et al. | |
| 2007/0225538 A1 | 9/2007 | Elomari | |
| 2013/0248423 A1* | 9/2013 | Serban et al. | 208/254 R |

FOREIGN PATENT DOCUMENTS

| | | |
|---|---|---|
| CN | 1943872 A | 4/2007 |
| CN | 1978431 A | 6/2007 |
| CN | 1978434 A | 6/2007 |
| CN | 101985435 A | 3/2011 |
| EP | 2520558 A1 | 11/2012 |

OTHER PUBLICATIONS

Zhang et al. (Journal of Molecular Catalysis A: Chemical (2014), 383-384, 101-105).*
Guo et al. (Dongbei Shiyou Daxue Xuebao (2012), 36(4), 64-67, 120). Abstract.*
Zhao et al. (CN 1944439), 2007. Abstract.*
Lin et al. (CN 101941986), 2011. Abstract.*
Yang et al., "Novel Ionic Liquid Crystals Based on N-Alkylcaprolactam as Cations," Chemistry Materials (2007), 19(10), 2544-2550.
Du et al., "Investigation of Physicochemical Properties of Lactam-Based Bronsted Acidic Ionic Liquids," Journal of Physical Chemistry B (2005), 109(41), 19542-19546.

Fabos et al., "e-Caprolactamium Hydrogen Sulfate: An Ionic Liquid Used for Decades . . . " ChemSusChem (2008), 1(3), 189-192.

(Continued)

*Primary Examiner* — Bruck Kifle

(57) ABSTRACT

Lactamium based ionic liquids are described. They comprise at least one of:
the reaction product of a lactam compound having a general formula

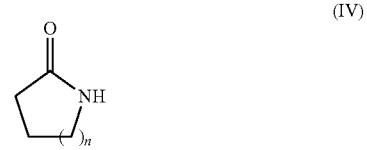

(IV)

wherein n is 1 to 8,
and a Brønsted acid HX; or a Brønsted acid HX, where X is a halide, and a metal halide; where the reaction product is p-toluenesulfonate, halide, or the halometallate;
or
the reaction product of a lactam compound having a general formula

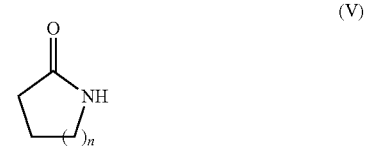

(V)

wherein the ring has at least C—C one double bond, and n is 1 to 8,
and a Brønsted acid HX; or a Brønsted acid HX, where X is a halide, and a metal halide;
or
the reaction product of a lactam compound having a general formula

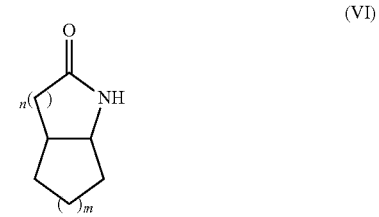

(VI)

wherein n is 1 to 8, m is 1 to 8, and the rings can be saturated or unsaturated;
and a Brønsted acid HX; or a Brønsted acid HX, where X is a halide, and a metal halide.

5 Claims, No Drawings

(56) References Cited

OTHER PUBLICATIONS

Guo et al., "Clean Beckmann rearrangement of cyclohexanone oxime in caprolactam-based Bronsted acidic ionic liquids", Green Chemistry (2006), vol. 8, 296-300.

Guo et al., "Absorption and Oxidation of H2S in Caprolactam Tetrabutyl Ammonium Bromide Ionic Liquid," Energy & Fuels (2011), vol. 25, 159-161.

Jiang et al., "Thermodynamic Properties of Caprolactam Ionic Liquids," Chinese Journal of Chemical Engineering (2013), 21(7), 766-769.

* cited by examiner

SYNTHESIS OF LACTAM BASED IONIC LIQUID

BACKGROUND OF THE INVENTION

Ionic liquids are of interest to industry because of their wide range of applications, including use as solvents and catalysts. Ionic liquids are salts comprised of cations and anions which typically melt below about 100° C.

Ionic liquids are described in U.S. Pat. Nos. 4,764,440, 5,104,840, and 5,824,832, for example. The properties vary extensively for different ionic liquids, and the use of ionic liquids depends on the properties of a given ionic liquid. Depending on the organic cation of the ionic liquid and the anion, the ionic liquid can have very different properties.

However, the cost of ionic liquids has limited the widespread adoption of ionic liquids.

There is a need for lower cost ionic liquids and for methods of making them.

SUMMARY OF THE INVENTION

One aspect of the invention is a lactamium based ionic liquid. In one embodiment, the ionic liquid has a general formula of at least one of:

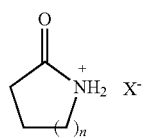

(I)

wherein n is 1 to 8, and $X^-$ is an anion group of a Brønsted acid HX or a halometallate, and wherein is $X^-$ is p-toluenesulfonate, halide, or the halometallate;

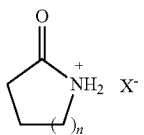

(II)

wherein the ring has at least one C—C double bond, n is 1 to 8, and $X^-$ is an anion group of a Brønsted acid HX or a halometallate;

or

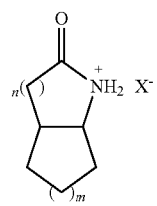

(III)

wherein n is 1 to 8, m is 1 to 8, $X^-$ is an anion group of a Brønsted acid HX or a halometallate, and the rings can be saturated or unsaturated.

In one embodiment, the lactamium based ionic liquid comprises at least one of:

the reaction product of a lactam compound having a general formula

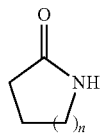

(IV)

wherein n is 1 to 8, and a Brønsted acid HX; or a Brønsted acid HX, where X is a halide, and a metal halide; where the reaction product is p-toluenesulfonate, halide, or the halometallate;

or the reaction product of a lactam compound having a general formula

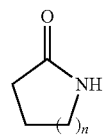

(V)

wherein the ring has at least one C—C double bond, and n is 1 to 8, and a Brønsted acid HX; or a Brønsted acid HX, where X is a halide, and a metal halide;

or the reaction product of a lactam compound having a general formula

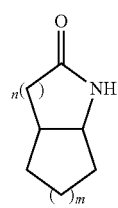

(VI)

wherein n is 1 to 8, m is 1 to 8, and the rings can be saturated or unsaturated;

and a Brønsted acid HX: or a Brønsted acid HX, where X is a halide, and a metal halide.

Another aspect of the invention is a method of making a lactamium based ionic liquid. In one embodiment, the method includes at least one of:

reacting a lactam compound having a general formula

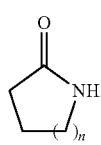

(IV)

wherein n is 1 to 8, with a Brønsted acid HX; or a Brønsted acid HX, where X is a halide, and a metal halide; where the reaction product is p-toluenesulfonate, halide, or the halometallate;

or reacting a lactam compound having a general formula

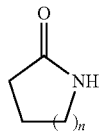
(V)

wherein the ring has at least one C—C double bond, and n is 1 to 8, with a Brønsted acid HX; or a Brønsted acid HX, where X is a halide, and a metal halide;

or reacting a lactam compound having a general formula

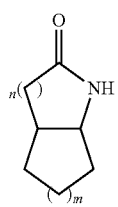
(VI)

wherein n is 1 to 8, m is 1 to 8, and the rings can be saturated or unsaturated;

with a Brønsted acid HX; or a Brønsted acid HX, where X is a halide, and a metal halide.

DETAILED DESCRIPTION OF THE INVENTION

The present invention provides cost effective ionic liquids capable of being produced on an industrial scale. The ionic liquids are lactamium based ionic liquids. Lactam compounds can be converted to ionic liquids through reactions with strong acids followed by a second reaction with a metal halide if needed. Lactamium based ionic liquids can be used in numerous applications and can have an economic benefit.

One type of lactamium based ionic liquid has the general formula:

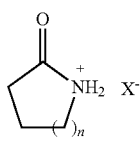
(I)

wherein n is 1 to 8, and $X^-$ is an anion group of a Brønsted acid HX or a halometallate, and wherein is $X^-$ is p-toluenesulfonate, halide, or the halometallate, with the proviso that when n is 3, $X^-$ is not a zinc halometallate.

Another way to represent this compound is:

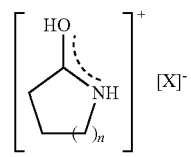

wherein n is 1 to 8, and $X^-$ is an anion group of a Brønsted acid HX or a halometallate, and wherein is $X^-$ is p-toluenesulfonate, halide, or the halometallate, with the proviso that when n is 3, $X^-$ is not a zinc halometallate.

Formula (I) is intended to cover both representations.

Suitable halides include, but are not limited to, bromide, chloride, and iodide.

Halometallates are mixtures of halides, such as bromide, chloride, and iodide, and metals. Suitable metals include, but are not limited to, Sn, Al, Zn, Mn, Fe, Ga, Cu, Ni, and Co. In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

Another type of lactamium based ionic liquid has the general formula:

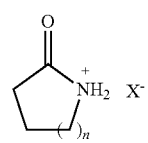
(II)

wherein the ring has at least one C—C double bond, n is 1 to 8, and $X^-$ is an anion group of a Brønsted acid HX or a halometallate.

The ring has at least one C—C double bond. Larger rings may have more than one C—C double bond. The C—C double bond(s) can be between any two adjacent carbons capable of forming a double bond.

Suitable $X^-$ groups include, but are not limited to, carboxylates, nitrates, phosphates, phosphinates, phosphonates, imides, cyanates, borates, sulfates (including bisulfates), sulfonates (including fluoroalkanesulfonates), acetates, halides, halometallates, and combinations thereof. Examples of $X^-$ groups include, but are not limited to, tetrafluoroborate, triflate, trifluoroacetate, chloroacetate, nitrate, hydrogen sulfate, hydrogen phosphate, dicyanoimide, methylsulfonate, and combinations thereof.

Another way to represent this compound is

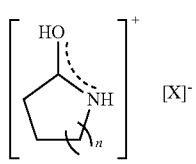

wherein the ring has at least one C—C double bond, n is 1 to 8, and $X^-$ is an anion group of a Brønsted acid HX or a halometallate.

Formula (II) is intended to cover both representations.

Examples of Formula (II) ionic liquids include, but are not limited to, 1,5-dihydro-pyrrol-2-one based ionic liquids, and 1,3-dihydro-2H-pyrrol-one based ionic liquids.

Another type of lactamium based ionic liquid has the general formula:

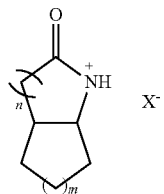

(III)

wherein n is 1 to 8, m is 1 to 8, X⁻ is an anion group of a Brønsted acid HX or a halometallate, and the rings can be saturated or unsaturated.

The heterocyclic ring (ring with n) can be saturated or unsaturated. The hydrocarbon ring (ring with m) can be saturated, unsaturated, or aromatic. If the ring is unsaturated, the C—C double bond can be between any two carbons capable of forming a double bond. There can be one or more C—C double bonds in either ring or in both rings.

Another way to represent this compound is

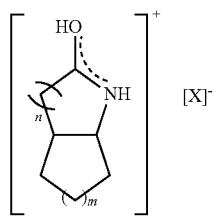

wherein n is 1 to 8, m is 1 to 8, X⁻ is an anion group of a Brønsted acid HX or a halometallate, and the rings can be saturated or unsaturated.

The heterocyclic ring (ring with n) can be saturated or unsaturated. The hydrocarbon ring (ring with m) can be saturated, unsaturated, or aromatic. If the ring is unsaturated, the C—C double bond can be between any two adjacent carbons capable of forming a double bond. There can be one or more C—C double bonds in either ring or in both rings.

Formula (III) is intended to cover both representations.

Examples of Formula (III) ionic liquids include, but are not limited to, octahydro-2H-indol-2-one ionic liquids, and 2-oxindole ionic liquids.

A lactamium based ionic liquid can be made by reacting a lactam compound having a general formula

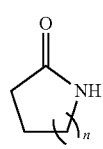

(IV)

wherein n is 1 to 8,
with a Brønsted acid HX; or a Brønsted acid HX where X is a halide, and a metal halide; where the reaction product is p-toluenesulfonate, halide, or the halometallate. In some embodiments, when n is 3, the reaction product is not a zinc halometallate.

Another lactamium based ionic liquid can be made by reacting a lactam compound having a general formula

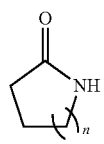

(V)

wherein the ring has at least one C—C double bond, and n is 1 to 8,
with a Brønsted acid HX; or a Brønsted acid HX, where X is a halide, and a metal halide.

Another lactamium based ionic liquid can be made by reacting a lactam compound having a general formula

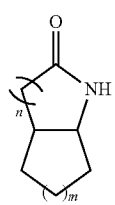

(VI)

wherein n is 1 to 8, m is 1 to 8, and the rings can be saturated or unsaturated;
with a Brønsted acid HX; or a Brønsted acid HX, where X is a halide, and a metal halide.

The heterocyclic ring (ring with n) can be saturated or unsaturated. The hydrocarbon ring (ring with m) can be saturated, unsaturated, or aromatic. If the ring is unsaturated, the C—C double bond can be between any two adjacent carbons capable of forming a double bond. There can be one or more C—C double bonds in either ring or in both rings.

In some embodiments, when making a halometallate, the lactam compound is reacted with a Brønsted acid HX, such as HCl, where X is a halide, to form a lactamium halide. The lactamium halide is then reacted with a halometallate to form the lactamium halometallate. In one embodiment, when a lactam compound having the general formula (I) and n is 3 is reacted, the lactam compound is reacted with a Brønsted acid HX, such as HCl, to form a lactamium halide. The lactamium halide is then reacted with a metal halide to form the lactamium halometallate.

As is understood by those of skill in the art, the particular Brønsted acid used will depend on the anion desired. Suitable Brønsted acids for use with lactam compound (IV) include for example, p-toluenesulfonic acid, hydrochloric acid, and hydrobromic acid. Suitable Brønsted acids HX for use with lactam compounds (V) and (VI) include, but are not limited to, at least one of sulfuric acid, p-toluenesulfonic acid, hydrochloric acid, hydrobromic acid, nitric acid, phosphoric acid, tetrafluoroboric acid, triflic acid, trifluoroacetic acid, chloroacetic acid, and methanesulfonic acid.

The reaction can take place at temperatures in the range of about −36° C. to the decomposition temperature of the ionic liquid, or about −20° C. to less than the decomposition temperature of the ionic liquid, or about 0° C. to about 200° C., or about 0° C. to about 150° C., or about 0° C. to about 120° C., or about 20° C. to about 80° C.

The reaction typically takes place at atmospheric pressure, although higher or lower pressures could be used if desired.

When making halometallate compounds, the reaction should take place in an inert atmosphere.

The reaction typically takes about 1 min to multiple days, depending on the ionic liquid. Those made with the Brønsted acid typically take minutes to hours, while the halometallates typically take minutes to one or more days.

The reaction may be practiced in laboratory scale experiments through full scale commercial operations. The process may be operated in batch, continuous, or semi-continuous mode.

Typically, the ratio of the Brønsted acid to the lactam compound is about 1:1 to about 3:1. In some embodiments, prior to making a halometallate, a lactamium halide is formed using a Brønsted acid, the ratio of Brønsted acid to the lactam compound is about 1:1.

In some embodiments, the reaction can take place in the absence of a solvent. In other embodiments, it can take place in the presence of a solvent. Suitable solvents for non-halometallate ionic liquids include, but are not limited to, water, toluene, dichloromethane, liquid carboxylic acids, such as acetic acid or propanoic acid, alcohols, such as methanol and ethanol, and combinations thereof. When water is used as the solvent, an additional product may form. The products can be separated using known separation techniques. Non-protic solvents, such as dichloromethane, are suitable for use with halometallates.

By the term "about," we mean within 10% of the value, or within 5%, or within 1%.

EXAMPLES

Example 1

Preparation of Caprolactamium p-toluenesulfonate

In a 20 mL vial, 1.05 g (9.2 mmol) of caprolactam was melted at 80° C. with stirring. p-toluene sulfonic acid monohydrate (9.0 mmol) was added to the caprolactam melt. After stirring for 0.75 h, volatiles were removed. Yield: 2.39 g (92.6%). The product was dissolved in dichloromethane, filtered, and volatiles were removed. $^1$H NMR (500 MHz, $d_6$-DMSO): 1.46-1.63 (m, 8H), 2.27 (s, 3H), 2.38 (t, 2H), 3.11 (t, 2H), 7.16 (d, 2H), 7.55 (d, 2H), 8.24 (broad s). $^{13}$C NMR (125 MHz, $d_6$-DMSO): 21.21, 22.95, 29.17, 30.08, 35.46, 42.28, 55.28, 125.91, 128.87, 139.32, 144.25, 179.44.

Example 2

Preparation of Caprolactamium Chloride

In a 100 mL round bottom flask, a HCl solution (24.84, 0.22 mol) was added to a toluene solution of caprolactam (25.05 g, 0.22 mol). After stirring for 2 hours at room temperature, the volatiles were removed. Yield: 34.2 g. The solid was dissolved in dichloromethane, filtered, and volatiles were removed. $^1$H NMR (500 MHz, $d_6$-DMSO): 1.49-1.64 (m, 6H), 2.35 (t, 2H), 3.08 (t, 2H), 7.90 (broad s). $^{13}$C NMR (125 MHz, $d_6$-DMSO): 23.31, 29.78, 30.40, 36.16, 42.25, 178.90.

Example 3

Preparation of Caprolactamium Chloroaluminate

All procedures were performed in a nitrogen glovebox. In a vial containing caprolactamium chloride (3.48 g, 0.23 mol), aluminum trichloride (6.37 g, 0.47 mol) was added slowly while stirring the mixture. After stirring for 5 hours, the mixture was allowed to settle and liquid was decanted. $^1$H NMR (500 MHz, CDCl$_3$): 1.85-1.94 (m, 6H), 2.90 (t, 2H), 3.63 (q, 2H), 8.07 (broad s). $^{13}$C NMR (125 MHz, CDCl$_3$): 23.31, 29.78, 30.40, 36.18, 42.24, 178.90.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A lactamium based ionic liquid comprising consisting at least of one of:

a reaction product of a lactam compound having a formula

(IV)

wherein n is 3, and a Brønsted acid HX; or a Brønsted acid HX, where X is a halide, and a metal halide; where the reaction product is a halide, or a halometallate.

2. A method of making a lactamium based ionic liquid comprising at least one of:

reacting a lactam compound having a formula

(IV)

wherein n is 3, with a Brønsted acid HX; or a Brønsted acid HX, where X is a halide, and a metal halide; where the reaction product is a halide, or a halometallate.

3. The method of claim 2 wherein the reaction takes place in a solvent.

4. The method of claim 3 wherein the solvent selected from the group consisting of water, toluene, dichloromethane, liquid carboxylic acids, alcohols, or combinations thereof.

5. The method of claim 2 wherein a ratio of the Brønsted acid HX to the lactam compound is about 1:1 to about 3:1.

* * * * *